United States Patent [19]
Fain et al.

[11] Patent Number: 5,730,141
[45] Date of Patent: Mar. 24, 1998

[54] TACHYARRHYTHMIA DETECTION METHOD

[75] Inventors: Eric S. Fain, Menlo Park; Lisa J. Malden, Palo Alto, both of Calif.

[73] Assignee: Pacesetter, Inc., Sunnyvale, Calif.

[21] Appl. No.: 660,299

[22] Filed: Jun. 7, 1996

[51] Int. Cl.$^6$ ................................................ A61B 5/0464
[52] U.S. Cl. ................................................ 128/705
[58] Field of Search ................................ 128/702–705; 364/413.06; 607/9, 5, 14

[56] References Cited

U.S. PATENT DOCUMENTS

| | | | |
|---|---|---|---|
| 3,593,705 | 7/1971 | Thomas et al. | 128/703 |
| 4,872,459 | 10/1989 | Pless et al. | 128/419 |
| 4,880,005 | 11/1989 | Pless et al. | 128/419 |
| 4,971,058 | 11/1990 | Pless et al. | 128/419 |
| 5,002,052 | 3/1991 | Haluska | 607/14 |
| 5,107,850 | 4/1992 | Olive | 128/705 |
| 5,350,406 | 9/1994 | Nitzsche et al. | 607/14 |
| 5,462,060 | 10/1995 | Jacobson et al. | 128/702 |
| 5,464,430 | 11/1995 | Rossing | 607/14 |
| 5,571,141 | 11/1996 | McNeil et al. | 607/5 |

*Primary Examiner*—William E. Kamm
*Attorney, Agent, or Firm*—Mark J. Meltzer; Steven M. Mitchell

[57] ABSTRACT

A method for detecting cardiac arrhythmias which includes the steps of detecting a patient's cardiac activity, counting the number of intervals which satisfy a first selected criterion, and producing a sinus interval history count indicative of the number of such intervals which are counted, making a preliminary diagnosis of tachyarrhythmia upon detecting that the cardiac activity satisfies a second selected criterion, and, making a final diagnosis of tachyarrhythmia if the sinus interval history count is less than a selected maximum sinus interval history count, and otherwise, inhibiting a final diagnosis of tachyarrhythmia. In an alternative embodiment, the method for detecting cardiac arrhythmias includes the steps of detecting a patient's cardiac activity, counting the number of intervals which satisfy a first selected criterion, and producing a sinus interval history count indicative of the number of such intervals which are counted, making a preliminary diagnosis of tachyarrhythmia upon detecting that the cardiac activity satisfies a second selected criterion, determining if the preliminary diagnosis of tachyarrhythmia is proper according to a first measure of interval irregularity, making a qualified preliminary diagnosis of tachyarrhythmia if it is determined that the preliminary diagnosis of tachyarrhythmia is proper according to the first measure of interval irregularity, and otherwise, inhibiting a final diagnosis of tachyarrhythmia, and, if a qualified preliminary diagnosis of tachyarrhythmia is made, then making a final diagnosis of tachyarrhythmia if the sinus interval history count is less than a selected maximum sinus interval history count, and otherwise, inhibiting a final diagnosis of tachyarrhythmia. The invention also includes a cardiac therapy device, e.g., an implantable cardioverter-defibrillator (ICD), programmed to implement the tachyarrhythmia detection method of the present invention.

17 Claims, 3 Drawing Sheets

TACHYARRHYTHMIA DETECTION METHOD

BACKGROUND OF THE INVENTION

The present invention relates generally to the field of cardiac therapy devices, particularly implantable cardioverter-defibrillators (ICDs), and more particularly, to a novel tachyarrhythmia detection (diagnostic) algorithm which can be employed in such devices for discriminating between ventricular and supraventricular tachyarrhythmias.

Implantable cardioverter defibrillators (ICDs) are highly sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle.

Cardiac arrhythmias can generally be thought of as disturbances of the normal rhythm of the heart beat. Cardiac arrhythmias are broadly divided into two major categories, namely, bradyarrhythmia and tachyarrhythmia. Tachyarrhythmia can be broadly defined as an abnormally rapid heart rate (e.g., over 100 beats/minute, at rest), and bradyarrhythmia can be broadly defined as an abnormally slow heart rate (e.g., less than 50 beats/minute). A normal cardiac rhythm (e.g., between 50–100 beats/minute) is referred to as a "sinus rhythm".

Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized.

Tachycardia and fibrillation are further classified according to their location within the heart, namely, either atrial or ventricular. In general, atrial arrhythmias are not life-threatening, because the atria (upper chambers of the heart) are only responsible for aiding the movement of blood into the ventricles (lower chambers of the heart), whereas ventricular arrhythmias are life-threatening, because if the ventricles become arrhythmic, the heart's ability to pump blood to the rest of the body is impaired. The most serious and immediately life-threatening type of cardiac arrhythmia is ventricular fibrillation, in which the electrical activity of the ventricles becomes so random and chaotic that the heart rapidly becomes unable to pump sufficient blood to sustain life.

In general, tachyarrhythmias which are ventricular in origin are referred to as "ventricular tachyarrhythmias", and tachyarrhythmias which are non-ventricular in origin are referred to as "supraventricular tachyarrhythmias" or "non-ventricular tachyarrhythmias". Supraventricular tachyarrhythmias encompass atrial tachycardia, atrial flutter, and atrial fibrillation.

In general, an ICD continuously monitors the heart activity of the patient in whom the device is implanted by analyzing electrical signals, known as electrograms (EGMs), generated by sensing electrodes positioned proximate the sino-atrial and/or atrio-ventricular node of the patient's heart, and, most advantageously, in the right ventricular apex of the patient's heart. More particularly, contemporary ICDs include waveform digitization circuitry which digitizes the analog EGM produced by the sensing electrodes, and a microprocessor and associated peripheral ICs which analyze the thusly digitized EGM in accordance with a diagnostic or detection algorithm implemented by software stored in the microprocessor. Contemporary ICDs are generally capable of diagnosing (detecting) the various types of cardiac arrhythmias discussed above, and then delivering the appropriate electrical energy/therapy to the patient's heart, in accordance with a therapy delivery algorithm also implemented in software stored in the microprocessor, to thereby convert or terminate the diagnosed arrhythmia.

In this connection, contemporary ICDs are capable of delivering various types or levels of electrical therapy. The first type of therapy is bradycardia and antitachycardia pacing, in which a low level of electrical energy (generally between millionths to thousandths of a joule) is delivered to the patient's heart in order to correct detected episodes of bradycardia or tachycardia, respectively. The second type of therapy is cardioversion, in which an intermediate level of electrical energy (generally between 1–5 joules) is delivered to the patient's heart in order to terminate a detected episode of ventricular arrhythmia (e.g., a detected heart beat in the range of 130–190 beats/minute) or an ongoing episode of tachycardia that antitachycardia pacing has failed to correct or abort. The third type of therapy is defibrillation, in which a high level of electrical energy (generally above 15 joules) is delivered to the patient's heart in order to terminate a detected episode of ventricular fibrillation or an episode of ventricular tachycardia which has degraded into ventricular fibrillation due to failure of cardioversion therapy.

The provision of the above-described different types or levels of therapy is oftentimes referred to in the art as "tiered therapy". In this regard, contemporary ICDs which are capable of delivering tiered therapy are sometimes referred to as combination pacemakers/defibrillators or as implantable cardioverter-defibrillators. As used herein, the terminology "implantable cardiac defibrillator" (ICD) is intended to encompass these and all other forms and types of implantable cardiac devices.

Current-generation ICDs which are capable of delivering tiered therapy provide several advantages over previous-generation ICDs which were only capable of delivering high energy defibrillation therapy. Namely, ICDs which are capable of delivering tiered therapy are generally more energy-efficient, since they can deliver much lower energy therapy, such as antitachycardia pacing and cardioversion, to terminate many arrhythmia events before they degrade into a ventricular fibrillation event. The much higher energy defibrillation therapy is only necessary when these lower energy therapies fail to terminate the arrhythmia. Thus, tiered therapy conserves the energy stored in the battery(ies) of the device, thereby extending the longevity of the device, and also enables a significant portion of potential ventricular fibrillation events to be terminated with lower energy therapy which is much less painful and uncomfortable to the patient.

In such ICDs which are capable of delivering tiered therapy, it is imperative that the detection or diagnostic algorithm employed be reliably accurate, so that the patient's heart condition can be accurately monitored at all times and any arrhythmias promptly and properly diagnosed and treated Coy delivery of the appropriate therapy to terminate or convert the detected arrhythmia). In this regard, there are a number of presently available or known detection algorithms which, for the most part, are quite reliable and accurate.

For example, U.S. Pat. No. 4,971,058, issued to Pless et al. and assigned to the assignee of the present invention, the disclosure of which is incorporated herein by reference, discloses a detection algorithm (hereinafter referred to as "the '058 detection algorithm") which determines the duration of the intervals between successive heartbeats (i.e., cycle lengths between consecutive QRS complexes), and computes a running average of the duration of a prescribed number (e.g., 4) of preceding intervals, referred to as the "average interval", which is re-computed (updated) every interval (i.e., on an interval-by-interval basis).

The '058 detection algorithm also classifies the spectrum of heart rates into several discrete bands which correspond to different cardiac conditions or rhythms. For example, a heart rate of <130 beats per minute could be classified as a normal sinus rhythm (SINUS), a heart rate of 130–160 beats per minute could be classified as a slow tachycardia rhythm (TACH A), a heart rate of 160–200 beats per minute could be classified as a fast tachycardia rhythm (TACH B), and a heart rate greater than 200 beats per minute could be classified as fibrillation (FIB). Since an interval duration can be extrapolated to heart beats per minute, it is apparent that a plurality of interval duration ranges can be selected which extrapolate to ("imply") the corresponding cardiac rhythm bands. On this basis, the detected intervals and average intervals are classified according the cardiac rhythm band corresponding to the interval duration range in which they fall. Thus, an interval (or average interval) that falls into an interval duration range (e.g., >450 msec) corresponding to normal sinus rhythm (SINUS) will be classified as a SINUS interval (or average interval), an interval (or average interval) that falls into an interval duration range (e.g., 380–450 msec) corresponding to slow (low rate) tachycardia (TACH A) will be classified as a TACH A interval (or average interval), an interval (or average interval) that falls into an interval range (e.g., 310–380 msec) corresponding to fast (high rate) tachycardia (TACH B) will be classified as a TACH B interval (or average interval), and an interval (or average interval) that falls into an interval duration range (e.g., <310 msec) corresponding to fibrillation (FIB) will be classified as a FIB interval (or average interval).

In accordance with the '058 detection algorithm, an arrhythmia is detected (diagnosed) in the following manner. More particularly, the RAM or other read/write memory of the device is organized into a plurality of different storage locations, referred to as temporary storage "bins", corresponding to the different cardiac rhythm bands into which the cardiac frequency spectrum is divided. Thus, there is a SINUS bin, a TACH A bin, a TACH B bin, and a FIB bin. At every interval, the determined interval duration and average interval are used (in accordance with the detection algorithm) to "bin" the interval, i.e., to increment the appropriate one of the bins. Each of the bins is assigned a maximum count limit. In this regard, the depth of each bin is determined by its programmed maximum count limit.

The '058 detection algorithm then determines when any of the bins has been counted up to its maximum count limit, i.e., is full. The '058 detection algorithm then returns or enters a diagnosis based on which bin first reaches its programmed maximum count limit. More particularly, if the SINUS bin is filled first, then the patient's cardiac condition is detected to be normal. If the FIB bin is filled first, then a diagnosis of fibrillation is made, and the appropriate defibrillation therapy subsequently delivered in accordance with the therapy delivery algorithm. If the TACH A bin is filled first, then a diagnosis of slow rate tachycardia is made, and the appropriate anti-tachycardia pacing or cardioversion delivered in accordance with the therapy delivery algorithm. If the TACH B bin is filled first, then a diagnosis of high rate tachycardia is made, and the appropriate cardioversion therapy delivered in accordance with the therapy delivery algorithm. An extended high rate (EHR) timer is also used to detect an EHR condition. When the EHR timer times out, a diagnosis of EHR is made, and defibrillation therapy is delivered in accordance with the therapy delivery algorithm. The EHR timer is cleared upon each diagnosis of a normal sinus rhythm or fibrillation. The arrhythmia bins are cleared (reset) upon each diagnosis of a tachyarrhythmia. All bins are cleared upon diagnosis of either a normal sinus rhythm or fibrillation.

The '058 detection algorithm also includes an algorithm section for discriminating between a tachycardia event and a bigeminal rhythm, by determining whether the total number of tachyarrhythmia intervals which were counted during the detection period (i.e., the combined count value of the TACH A, TACH B, and FIB bins) was greater than the total number of sinus intervals which were counted during the detection period (i.e., the count value in the SINUS bin). If the number of tachycardia intervals which were counted during the detection period is not greater than the number of sinus intervals which were counted during the detection period, then the arrhythmia diagnosis is inhibited. Thus, the '058 detection algorithm keeps track of the relative number of sinus intervals and tachycardia intervals during the detection period to prevent a bigeminal rhythm from being inappropriately diagnosed as tachycardia. However, although this "measure of interval altemans" is effective to adequately discriminate between tachycardia and a bigeminal rhythm, it is not capable of reliably distinguishing or discriminating between ventricular and supraventricular tachyarrhythmias, so that the appropriate therapy (or no therapy) can be delivered, for the reasons developed below.

More particularly, ventricular tachyarrhythmias are generally characterized by a large number of consecutive ventricular tachyarrhythmia intervals, and rarely, if ever, during an actual episode of ventricular tachyarrhythmia will there be more than a few (e.g., 1–3) intervening sinus intervals. On the other hand, some supraventricular tachyarrhythmias, in particular atrial fibrillation, are generally more sporadic, in that sinus intervals are typically interspersed with tachyarrhythmia intervals. Thus, atrial fibrillation is generally characterized by variable intervals or interval irregularity. This property of beat-to-beat variation in ventricular intervals during atrial fibrillation has previously been used in an attempt to distinguish atrial fibrillation from ventricular tachycardia. However, in some instances, the intervals may regularize to the extent that a fairly large number of stable tachyarrhythmia intervals occur. If this phenomenon occurs during the detection period or window, then it is quite apparent that an episode of supraventricular tachyarrhythmia could be misdiagnosed as an episode of ventricular arrhythmia.

Obviously, a misdiagnosis of supraventricular tachyarrhythmia as ventricular tachyarrhythmia would result in a subsequent delivery of therapy (treatment) which is inappropriate. If therapy is delivered that is not required it may actually induce an arrhythmia that really does require treatment, and, at a minimum, will result in a waste of the finite amount of energy that the device is capable of delivering over its lifetime, thereby shortening its useful lifetime.

Based on the above, although the presently available detection algorithms such as the '058 detection algorithm discussed above are generally quite sensitive and reliable in detecting ventricular arrhythmias, there still exists a need in the art for a detection method (and cardiac therapy device for implementing the same) which reliably discriminates between ventricular and supraventricular arrhythmias, thereby improving detection specificity. The present invention fulfills this need in the art.

SUMMARY OF THE INVENTION

The present invention encompasses a method for detecting cardiac arrhythmias which includes the steps of detecting a patient's cardiac activity, counting the number of intervals which satisfy a first selected criterion, and producing a sinus interval history count indicative of the number of such intervals which are counted, making a preliminary diagnosis of tachyarrhythmia upon detecting that the cardiac activity satisfies a second selected criterion, and, making a final diagnosis of tachyarrhythmia if the sinus interval history count is less than a selected maximum sinus interval history count, and otherwise, inhibiting a final diagnosis of tachyarrhythmia.

The present invention also encompasses a method for detecting cardiac arrhythmias which includes the steps of detecting a patient's cardiac activity, counting the number of intervals which satisfy a first selected criterion, and producing a sinus interval history count indicative of the number of such intervals which are counted, making a preliminary diagnosis of tachyarrhythmia upon detecting that the cardiac activity satisfies a second selected criterion, determining if the preliminary diagnosis of tachyarrhythmia is proper according to a first measure of interval irregularity, making a qualified preliminary diagnosis of tachyarrhythmia if it is determined that the preliminary diagnosis of tachyarrhythmia is proper according to the first measure of interval irregularity, and otherwise, inhibiting a final diagnosis of tachyarrhythmia, and, if a qualified preliminary diagnosis of tachyarrhythmia is made, then making a final diagnosis of tachyarrhythmia if the sinus interval history count is less than a selected maximum sinus interval history count, and otherwise, inhibiting a final diagnosis of tachyarrhythmia.

In a first preferred embodiment, the method of the present invention includes the steps of monitoring an electrogram representative of a patient's cardiac activity, sensing intervals between successive cardiac events, at every interval, determining the duration of that interval and computing the average duration of a prescribed number of preceding intervals, including that interval, initiating a detection period upon detecting that the computed average duration is less than a prescribed average duration threshold, at every interval after initiation of the detection period, classifying that interval as either a countable tachyarrhythmia interval or a countable sinus interval, based upon the determined duration of that interval and the computed average duration associated with that interval, and further classifying that interval as an absolute sinus interval if either the duration of that interval or the computed average duration associated with that interval is greater than a prescribed duration threshold, counting the number of absolute sinus intervals, counting the number of countable tachyarrhythmia intervals and countable sinus intervals, terminating the detection period and making a preliminary diagnosis of tachyarrhythmia if the counted number of countable tachyarrhythmia intervals exceeds a prescribed maximum tachyarrhythmia count before the counted number of countable sinus intervals exceeds a prescribed maximum sinus interval count, and, making a final diagnosis of tachyarrhythmia if the counted number of absolute sinus intervals during the detection period is less than a prescribed maximum absolute sinus interval count, and otherwise, inhibiting diagnosis of tachyarrhythmia.

In a second preferred embodiment, the method of the present invention includes the steps of monitoring an electrogram representative of a patient's cardiac activity, sensing intervals between successive cardiac events, at every interval, determining the duration of that interval and computing the average duration of a prescribed number of preceding intervals, including that interval, and classifying that interval as either a countable tachyarrhythmia interval or a countable sinus interval, based upon the determined duration of that interval and the computed average duration associated with that interval, and further classifying that interval as an absolute sinus interval if either the duration of that interval or the computed average duration associated with that interval is greater than a prescribed duration threshold, counting the number of absolute sinus intervals, counting the number of countable tachyarrhythmia intervals and countable sinus intervals, terminating the tachyarrhythmia detection period and making a preliminary diagnosis of tachyarrhythmia if the counted number of countable tachyarrhythmia intervals exceeds a prescribed maximum tachyarrhythmia count before the counted number of countable sinus intervals exceeds a prescribed maximum sinus interval count, and determining if the preliminary diagnosis of tachyarrhythmia is proper according to a first measure of interval irregularity, making a qualified preliminary diagnosis of tachyarrhythmia if it is determined that the preliminary diagnosis of tachyarrhythmia is proper according to the first measure of interval irregularity, and otherwise, inhibiting a final diagnosis of tachyarrhythmia, and, if a qualified preliminary diagnosis of tachyarrhythmia is made, then making a final diagnosis of tachyarrhythmia if the counted number of sinus intervals during the tachyarrhythmia detection period is less than a selected maximum sinus interval count, and otherwise, inhibiting a final diagnosis of tachyarrhythmia.

In an alternative embodiment which can be implemented with either of the above embodiments, the sinus interval history technique can be applied to just a rate overlap zone. Thus, after the initial diagnosis based on rate, the rate average is compared to a higher tachycardia threshold defining a rate overlap zone. If the average falls within the zone then the algorithm of the algorithm of the invention continues. If the average is greater than the rate overlap zone then a ventricular tachycardia is diagnosed.

The present invention also encompasses a cardiac therapy device, e.g., an implantable cardioverter-defibrillator (ICD), programmed to implement the tachyarrhythmia detection method of the present invention.

BRIEF DESCRIPTION OF THE DRAWINGS

These and various other features and advantages of the present invention will be more clearly understood from the following detailed description taken in conjunction with the accompanying drawings, in which.

DETAILED DESCRIPTION OF THE INVENTION

Figure 1:
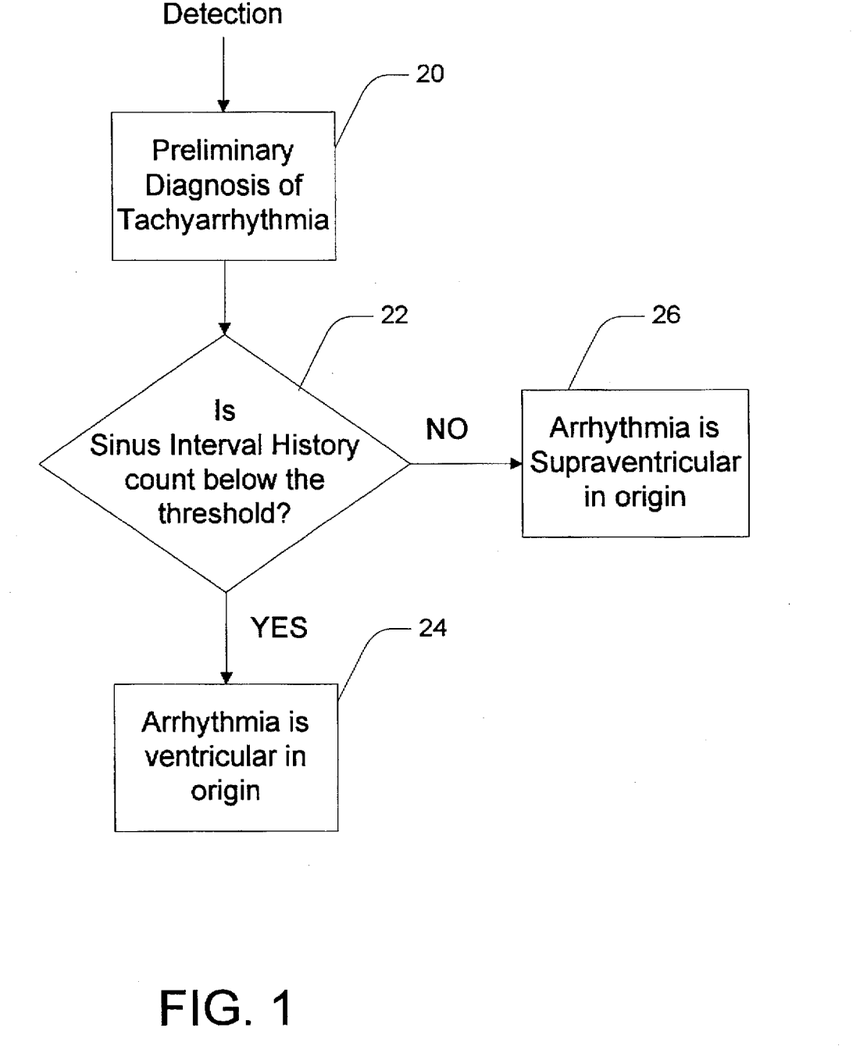
FIG. 1 is a flow chart illustrating the detection method of the present invention used to provide a stand-alone measure of interval irregularity which enables discrimination between ventricular and supraventricular tachyarrhythmias.
Figure 2:
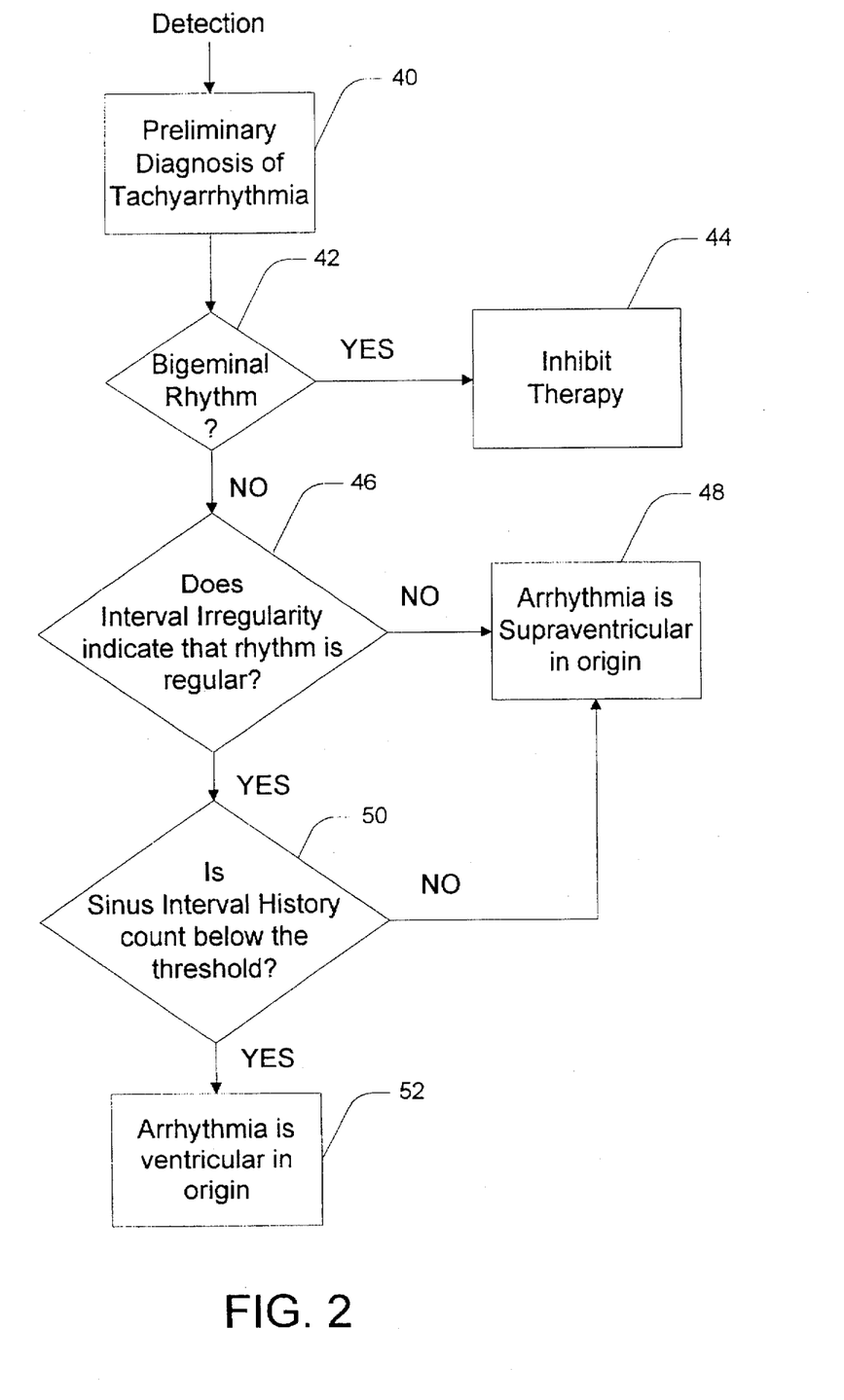
FIG. 2 is a flow chart illustrating the detection method of the present invention used in conjunction with a conventional detection algorithm which provides a first measure of interval irregularity, to provide a second measure of interval irregularity which enables discrimination between ventricular and supraventricular tachyarrhythmias.

In overview, the present invention encompasses a novel detection algorithm which can be used in conjunction with a conventional diagnosis algorithm which can be used to provide a stand-alone measure of interval irregularity which enables discrimination between ventricular and supraventricular tachyarrhythmias (as is depicted in FIG. 1), or which provides a first measure of interval irregularity for qualifying a diagnosis of tachyarrhythmia, in order to provide a second measure of interval irregularity which enables discrimination between ventricular and supraventricular tachyarrhythmias (as is depicted in FIG. 2). For example, the novel detection algorithm of the present invention can be used to independently qualify a cardiac episode which has been preliminarily diagnosed as a tachyarrhythmia as being either a ventricular or supraventricular tachyarrhythmia; or, alteratively, the novel detection algorithm of the present invention can be used to further qualify a cardiac episode which has already been diagnosed (preliminarily) as a tachyarrhythmia (by a diagnosis algorithm) and which has already been qualified in accordance with a first measure of interval irregularity as being a regular tachyarrhythmia, as either a ventricular or supraventricular tachyarrhythmia.

The present invention is basically premised upon the fact that during an episode of ventricular tachycardia most, if not all, intervals between successive heartbeats are tachycardia (non-sinus) intervals, and that consequently, it is possible to inhibit a diagnosis of ventricular tachycardia by determining whether more than a selected small number of sinus intervals or sinus average intervals occur during a detection period (window) in which the conventional ventricular tachyarrhythmia diagnosis criteria are met.

At the outset, it should be clearly understood that the specific diagnosis algorithm used in conjunction with the detection algorithm of the present invention is not limiting to the present invention, i.e., any convenient diagnostic algorithm can be used. In general, the detection algorithm of the present invention is employed to qualify a preliminary diagnosis of ventricular tachyarrhythmia made in any suitable manner, in order to inhibit the diagnosis if a prescribed criterion (discussed hereinbelow) is satisfied. In this connection, for ease of illustration of the present invention, it will be assumed that the '058 diagnosis algorithm described hereinabove is employed in order to make a preliminary diagnosis of tachyarrhythmia, although this is obviously not limiting to the present invention, in its broadest aspect.

As was described previously, the '058 diagnostic algorithm classifies each interval between successive heartbeats according to the duration of the interval and the computed interval average (calculated using the most recent four (or other prescribed number) interval durations). A detection period (window) is started when a prescribed initial condition is met, namely, that the computed interval and interval average are in the tachyarrhythmia range. After the detection period is commenced, each subsequent interval is binned according to the duration of the interval and the computed interval average associated with the interval, i.e., the appropriate bin is incremented based upon the classification of the interval. The diagnostic algorithm terminates the detection period and makes a preliminary diagnosis when any of the bins is filled, the diagnosis being based upon which of the bins is filled first.

If the preliminary diagnosis is tachyarrhythmia, then the '058 detection algorithm qualifies the diagnosis (i.e., verifies the accuracy of the preliminary diagnosis) by using a measure of interval alternans, namely, the relative number of sinus intervals and tachyarrhythmia intervals, to discriminate a bigeminal rhythm from a tachyarrhythmia. In particular, if the number of tachycardia intervals counted during the detection period is not greater than the number of sinus intervals which were counted during the detection period by some prescribed value ("bigeminal avoidance criteria"), then the rhythm is considered a bigeminal rhythm. The detection algorithm may also determine whether the detected rhythm is regular or irregular (i.e., provides a "measure of interval irregularity"), e.g., by looking at beat-to-beat variations. If the rhythm is determined to satisfy either the bigeminal avoidance criteria or the measure of interval irregularity criterion (i.e., is determined to be irregular), a final diagnosis of tachyarrhythmia is inhibited.

In accordance with the detection method of the present invention, each interval is further classified as an absolute sinus interval if either the duration of that interval or the associated interval average is in the sinus range, e.g., greater than a prescribed sinus duration threshold. Further, the number of absolute sinus intervals are counted, with the count being initialized when the first tachyarrhythmia interval is binned (i.e., at the beginning of each detection period) and reset at the end of each detection period. If the number of absolute sinus intervals which are counted during the detection period (hereinafter referred to as the "sinus interval history" (SIH) count) is greater than a selected small number (e.g., 1–8), then the detected rhythm is considered to be a supraventricular arrhythmia, and a final diagnosis of tachyarrhythmia is inhibited. (If the detection method of the present invention is used in conjunction with a "first measure of interval irregularity", as opposed to being implemented as a stand-alone/independent measure of interval irregularity, then it must also be determined that the rhythm is regular in accordance with the "first measure of interval irregularity"). In this regard, any convenient hardware or software counter can be used to count the absolute sinus intervals, as will be readily apparent to those of ordinary skill in the pertinent art.

Thus, the detection method of the present invention can be used when a preliminary diagnosis of tachyarrhythmia is made in order to discriminate between ventricular and supraventricular tachyarrhythmia, and thereby prevent an improper diagnosis of tachyarrhythmia and delivery of therapy for tachyarrhythmia when such is not warranted. In this sense, the detection method of the present invention can be considered as providing a measure of interval irregularity (the SIH count) which can be used independently to qualify a diagnosis of tachyarrhythmia, or which can be used as an additional measure of interval irregularity to further qualify a diagnosis of tachyarrhythmia that has already been qualified as correct according a first measure of interval irregularity.

With reference now to FIG. 1, there can be seen a flow chart illustrating the detection method of the present invention used to provide a stand-alone measure of interval irregularity which enables discrimination between ventricular and supraventricular tachyarrhythmias. More particularly, a preliminary diagnosis of tachyarrhythmia is made, at step 20, (e.g., by a conventional diagnosis algorithm). The preliminary diagnosis of tachycardia may include a bigeminal avoidance step in accordance with the '058 detection algorithm. After preliminary diagnosis of tachycardia, the algorithm proceeds to step 22, in which it is determined whether the SIH count is below the selected SIH count threshold (e.g., 1–8). If yes, then the algorithm proceeds to step 24, and indicates that the tachyarrhythmia is ventricular in origin. If not, then the algorithm goes to step 26, and indicates that the tachyarrhythmia is supraventricular in origin. Thus, in this embodiment of the present invention, the SIH count is used as a stand-alone measure of interval irregularity in order to qualify the preliminary diagnosis of tachyarrhythmia, i.e., to confirm (verify) that a diagnosis of tachyarrhythmia is proper, or to determine that a diagnosis of tachyarrhythmia is improper.

With reference now to FIG. 2, there can be seen a flow chart illustrating the detection method of the present invention used in conjunction with a conventional diagnosis algorithm which provides both bigeminal avoidance and a first measure of interval irregularity. More particularly, after a preliminary diagnosis of tachyarrhythmia has been made, at step 40, (e.g., by a conventional diagnosis algorithm), the algorithm proceeds to step 42, in which it determines if the rhythm is a bigeminal rhythm as discussed in connection with the '058 detection algorithm. If it is determined that a bigeminal rhythm is present, diagnosis of a tachycardia is inhibited at step 44. If the rhythm is not bigeminal, the algorithm proceeds to step 46, in which it determines whether a first measure of interval irregularity indicates whether the preliminarily diagnosed tachyarrhythmia is "regular" (i.e., may be ventricular in origin) or is irregular (e.g., atrial fibrillation). If the preliminarily diagnosed tachyarrhythmia is determined to be "irregular" according to the first measure of interval irregularity, then the algorithm proceeds to step 48, and indicates that the tachyarrhythmia is supraventricular in origin. If the preliminarily diagnosed tachyarrhythmia is determined to be "regular" according to the first measure of interval irregularity, then, in accordance with the present invention, the algorithm proceeds to step 50, in which it is determined whether the SIH count is below the selected SIH count threshold (e.g., 1–8). If yes, then the algorithm proceeds to step 52, and indicates that the tachyarrhythmia is "regular", i.e., ventricular in origin. If not, then the algorithm goes to step 48, and indicates that the tachyarrhythmia is supraventricular in origin. Thus, in this embodiment of the present invention, the SIH count is used as a second measure of interval irregularity in order to further qualify the preliminary diagnosis of tachyarrhythmia, i.e., to confirm (verify) that a diagnosis of tachyarrhythmia is proper, or to determine that a diagnosis of tachyarrhythmia is improper. It should be noted that the embodiment of FIG. 2 can also be implemented without the bigeminal avoidance step 42.

In an alternative embodiment which can be used with the embodiment of either FIG. 1 or FIG. 2, the SIH test is applied only if the tachyarrhythmia falls within a rate overlap zone. Thus, if the average associated with the last tachyarrhythm is interval is shorter than a rate overlap threshold and thus falls outside the rate overlap zone, a final diagnosis of a tachyarrhythmia of ventricular origin is given. However, if the average duration is greater than the rate overlap threshold and shorter than the tachyarrhythmia threshold, then the SIH count is used to provide a final diagnosis in accordance with the description above.

Figure 3:
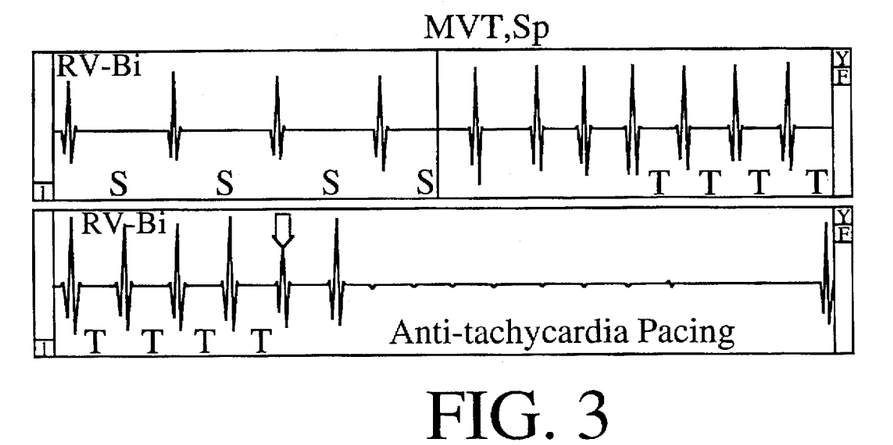
FIG. 3 is a diagram depicting an electrogram which exhibits a sinus rhythm which spontaneously converts to a monomorphic ventricular tachycardia (MVT), with the intervals between successive heartbeats which are binned as sinus intervals being designated "S" and the intervals between successive heartbeats which are binned as tachycardia intervals being designated "T"; and, FIG. 4 is a diagram depicting an electrogram which exhibits an episode of atrial fibrillation, with the intervals between successive heartbeats which are binned as sinus intervals being designated "S" and the intervals between successive heartbeats which are binned as tachycardia intervals being designated "T".
Figure 4:
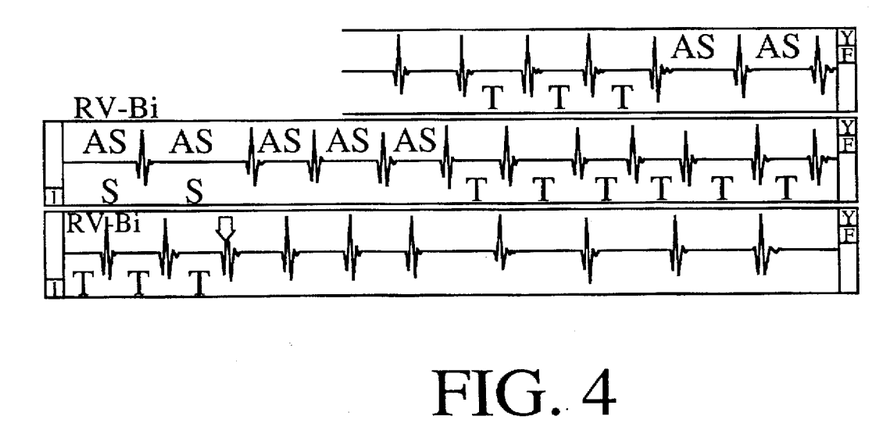

With reference now to FIGS. 3 and 4, the operation of the detection method of the present invention with respect to two different cases will now be described (it first will be assumed that the stand-alone embodiment of the detection method of the present invention is employed). For ease of illustration it will be assumed that the '058 diagnostic algorithm is used in both cases. With particular reference now to FIG. 3, there can be seen an electrogram which exhibits a sinus rhythm which spontaneously converts to a monomorphic ventricular tachycardia (MVT), with the intervals between successive heartbeats which are binned as sinus intervals being designated "S" and the intervals between successive heartbeats which are binned as tachycardia intervals being designated "T".

As can be seen in FIG. 3, after four intervals whose duration and associated interval average fall within the sinus zone, and which are thus binned as sinus intervals ("S"), the rhythm spontaneously converts to a monomorphic ventricular tachyarrhythmia (MVT). During the first three intervals following the commencement of the tachyarrhythmia, the interval duration falls within the tachycardia zone, but the interval average remains within the sinus zone, and thus, none of these intervals are binned as tachycardia intervals. By the fourth interval following the commencement of the tachyarrhythmia, the interval average has reached the tachycardia zone, and the subsequent intervals that have a duration which falls within the tachycardia zone are binned as tachycardia intervals ("T"). It will be assumed that eight consecutive tachycardia intervals ("T") satisfy the criterion for tachyarrhythmia detection. Thus, after eight consecutive T intervals, a preliminary diagnosis of tachyarrhythmia is made, as indicated by the downwardly pointing arrow in FIG. 3. This step can further include application of the bigeminal avoidance criterion.

In accordance with the present invention, the SIH count is reset (initialized to zero) when the first interval (T) which is binned as a tachycardia interval occurs. Thereafter, until the preliminary diagnosis of tachyarrhythmia is made (at which time the detection period is terminated), the number of absolute sinus intervals is counted in the manner described hereinbefore. More particularly, all intervals whose duration or associated interval average falls within the sinus zone are classified as absolute sinus intervals (AS). In the case of the cardiac episode (MVT) depicted in FIG. 3, since all intervals which occur during the detection period are binned as tachycardia intervals T, (i.e., eight consecutive T intervals occur), the SIH count is not incremented, and thus, is zero (0) at the time the preliminary diagnosis is made. Thus, in accordance with the present invention, it will be determined that the SIH count is below the selected maximum SIH count threshold (e.g., 2), and the preliminary diagnosis of tachyarrhythmia will be verified as proper, a final diagnosis of tachyarrhythmia made. Of course, the appropriate therapy will be delivered in the normal manner to terminate the diagnosed tachyarrhythmia, as seen in FIG. 3 with the delivery of antitachycardia pacing therapy.

The outcome would be unchanged if a preliminary interval irregularity step (as shown in FIG. 2) were applied to the rhythm of FIG. 3. In that case, for example, the duration of a prescribed number of intervals during the tahcyarrhythmia detection period preceding the preliminary diagnosis of tachyarrhythmia detection are considered. The longest and shortest of these intervals are discarded, the difference between the duration of the second longest and second shortest is calculated and this difference is compared to a selected delta. If the difference is greater than or equal to the delta, the rhythm is considered irregular. If the difference is shorter than the delta, the rhythm is considered regular. In FIG. 3, if the prescribed number of intervals is for example 8, it can be easily seen that the difference between the second longest and second shortest interval would be less than a typical selected delta and the preliminary interval irregularity measure would indicate that the rhythm would be considered regular. Examination of the second measure of interval irregularity, SIH, would confirm the rhythm as regular. It should be noted that other interval irregularity or rate stability tests known in the art could be used.

With particular reference now to FIG. 4, there can be seen an electrogram which exhibits an episode of atrial fibrillation (AF), which is a type of supraventricular tachyarrhythmia. Again, the intervals which are binned as sinus intervals are designated "S", the intervals which are binned as tachycardia intervals are designated "T", and the intervals which are classified as absolute sinus intervals are designated "AS". As can be seen in FIG. 4, three consecutive intervals T which are binned as tachycardia intervals are followed by two intervals which have a duration which falls within the sinus zone but which are not binned as either sinus or tachycardia intervals, which two intervals are in turn followed by two intervals S which are binned as sinus intervals. The two binned sinus intervals S are then followed by three consecutive intervals which have a duration which falls within the tachycardia zone, but which are not binned as tachycardia intervals, since the associated interval averages fall in the sinus zone. These three unbinned intervals are followed by nine (9) consecutive intervals which are binned as tachycardia intervals T.

It will be assumed that a total of twelve tachycardia intervals ("T") satisfy the criterion for tachyarrhythm is detection, and that a total of three sinus intervals ("S") satisfy the criterion for sinus rhythm detection. Thus, after twelve T intervals, a preliminary diagnosis of tachyarrhythmia is made, as indicated by the downwardly pointing arrow in FIG. 4, since the tachyarrhythmia detection criterion is met before the sinus rhythm detection criterion is met, i.e., the tachyarrhythmia bin is filled before the sinus bin is filled.

In accordance with the present invention, the SIH count is reset (initialized to zero) when the first interval (T) which is binned as a tachycardia interval occurs. Thereafter, until the preliminary diagnosis of tachyarrhythmia is made (at which time the detection period is terminated), the number of absolute sinus intervals is counted in the manner described hereinbefore. More particularly, all intervals whose duration or associated interval average falls within the sinus zone are classified as absolute sinus intervals "AS". In the case of the cardiac event (AF) depicted in FIG. 4, a total of seven (7) intervals are classified as absolute sinus intervals AS. Thus, in accordance with the present invention, it will be determined that the SIH count is above the selected maximum SIH count threshold (e.g., 2), and the preliminary diagnosis of tachyarrhythmia will not be verified as proper, i.e., the tachyarrhythmia will be identified as non-ventricular in origin, and a diagnosis of tachyarrhythmia will be inhibited. Thus, no therapy will be delivered.

It should be noted that presently available measures of interval irregularity would not enable the atrial fibrillation to be identified as supraventricular in origin in the above-described case depicted in FIG. 4, since the atrial fibrillation rhythm had stable intervals according to more typical measures of irregularity during the detection window. Thus, using presently available detection algorithms, an improper final diagnosis of tachyarrhythmia would have been returned in this case.

With continuing reference to FIGS. 3 and 4, the operation of the detection method of the present invention with respect to the two different cases will now be described for the embodiment of the detection method utilizing a preliminary interval irregularity measure followed by the SIH measure. It will be assumed that the '058 diagnostic algorithm is used in both cases as discussed above with reference to the stand-alone embodiment. With particular reference now to FIG. 3, there can be seen an electrogram which exhibits a sinus rhythm which spontaneously converts to a monomorphic ventricular tachycardia (MVT), with the intervals between successive heartbeats which are binned as sinus intervals being designated "S" and the intervals between successive heartbeats which are binned as tachycardia intervals being designated "T".

As can be seen in FIG. 3, after four intervals whose duration and associated interval average fall within the sinus zone, and which are thus binned as sinus intervals ("S"), the rhythm spontaneously converts to a monomorphic ventricular tachyarrhythmia (MVT). After eight consecutive T intervals, a preliminary diagnosis of tachyarrhythmia is made, as indicated by the downwardly pointing arrow in FIG. 3. A bigeminal avoidance criterion is applied but since there were no sinus intervals detected after initiation of the tachycardia detection period the rhythm is not bigeminal. Next, the preliminary interval irregularity criterion is applied. As discussed above, this can be any of the interval irregularity tests known in the art and the particular test is not part of the present invention. Using the technique described hereinabove, a window of the 8 intervals preceding the preliminary tachyarrhythmia diagnosis is considered and the difference between the second longest and second shortest of these intervals is compared with the selected delta. The test indicates a regular rhythm.

The SIH count is reset (initialized to zero) when the first interval (T) which is binned as a tachycardia interval occurs. Thereafter, until the preliminary diagnosis of tachyarrhythmia is made (at which time the detection period is terminated), the number of absolute sinus intervals is counted in the manner described hereinbefore. Since, in FIG. 3, all intervals which occur during the detection period are binned as tachycardia intervals T, (i.e., eight consecutive T intervals occur), the SIH count is not incremented, and thus, is zero (0) following the preliminary diagnosis, bigeminal avoidance test and the preliminary interval irregularity determination. Thus, in accordance with the present invention, it will be determined that the SIH count is below the selected maximum SIH count threshold (e.g., 2), and the preliminary diagnosis of tachyarrhythmia will be verified as proper, a final diagnosis of tachyarrhythmia made.

With particular reference now to FIG. 4, there can be seen an electrogram which exhibits an episode of atrial fibrillation (AF), which is a type of supraventricular tachyarrhythmia. Again, the intervals which are binned as sinus intervals are designated "S", the intervals which are binned as tachycardia intervals are designated "T", and the intervals which are classified as absolute sinus intervals are designated "AS". As can be seen in FIG. 4, three consecutive intervals T which are binned as tachycardia intervals are followed by two intervals which have a duration which falls within the sinus zone but which are not binned as either sinus or tachycardia intervals, which two intervals are in turn followed by two intervals S which are binned as sinus intervals. The two binned sinus intervals S are then followed by three consecutive intervals which have a duration which falls within the tachycardia zone, but which are not binned as tachycardia intervals, since the associated interval averages fall in the sinus zone. These three unbinned intervals are followed by nine (9) consecutive intervals which are binned as tachycardia intervals T.

It will be assumed that a total of twelve tachycardia intervals ("T") satisfy the criterion for tachyarrhythmia detection, and that a total of three sinus intervals ("S") satisfy the criterion for sinus rhythm detection. Thus, after twelve T intervals, a preliminary diagnosis of tachyarrhythmia is made, as indicated by the downwardly pointing arrow in FIG. 4, since the tachyarrhythmia detection criterion is met before the sinus rhythm detection criterion is met, i.e., the tachyarrhythmia bin is filled before the sinus bin is filled.

In accordance with the second embodiment of the present invention, the bigeminal avoidance test is applied and determines that the rhythm is not bigeminal since the number of sinus intervals does not equal the number of tachyarrhythmia intervals. Next the preliminary interval irregularity test is applied. Whether this test indicates a regular rhythm or not is a function of the particular test applied and its programmed sensitivity. For purposes of illustration, we will use 12 intervals for the window and a delta of 50 reset. The difference between the second longest and second shortest of the 12 intervals preceding the preliminary tahcyarrhythmia diagnosis is compared with the selected delta. The difference is smaller than the delta and the preliminary interval irregularity test determines a regular interval. The SIH count is reset (initialized to zero) when the first interval (T) which is binned as a tachycardia interval occurs. Thereafter, until the preliminary diagnosis of tachyarrhythmia is made (at which time the detection period is terminated), the number of absolute sinus intervals is counted in the manner described hereinbefore. More particularly, all intervals whose duration or associated interval average falls within the sinus zone are classified as absolute sinus intervals "AS". In the case of the cardiac event (AF) depicted in FIG. 4, a total of seven (7) intervals are classified as absolute sinus intervals AS. Thus, in accordance with the present invention, it will be determined that the SIH count is above the selected maximum SIH count threshold (e.g., 2), and the preliminary diagnosis of tachyarrhythmia and preliminary interval irregularity tests will not be verified as proper, i.e., the tachyarrhythmia will be identified as non-ventricular in origin, and a diagnosis of tachyarrhythmia will be inhibited. Thus, no therapy will be delivered.

It will be readily appreciated by those skilled in the pertinent art that the present invention also encompasses a cardiac therapy device, e.g., an ICD, programmed to implement the tachyarrhythmia detection method of the present invention. In this regard, it is a routine matter to those of ordinary skill in the pertinent art to write the code constituting the software (computer program) for programming the ICD (or other cardiac therapy device), using readily available programming tools. Further, although the detection algorithm has been described hereinabove in terms of sensing intervals between successive heartbeats, it should be clearly understood that the term "heartbeats" is intended in a generic sense to mean "cardiac events", e.g., QRS complexes. Additionally, the particular hardware and/or software used to count or bin intervals that are "countable" or "binnable" in accordance with the detection algorithm employed, and/or to count absolute sinus intervals to generate the SIH count, is not limiting to the present invention, as will be readily apparent to those of ordinary skill in the pertinent art.

Although the present invention has been described in detail hereinabove, it should be clearly understood that many variations and/or modifications of the basic inventive concepts herein taught which may appear to those skilled in the pertinent art will still fall within the spirit and scope of the present invention, as defined in the appended claims.

What is claimed is:

1. A method for detecting cardiac arrhythmias, including the steps of:

detecting a patient's cardiac activity and initiating a tachyarrhythmia detection period upon detecting that the cardiac activity satisfies a first selected tachyarrhythmia criterion;

counting the number of intervals which satisfy a second selected tachyarrhythmia criterion, and producing a sinus interval history count indicative of the number of such intervals which are counted;

terminating the tachyarrhythmia detection period and making a preliminary diagnosis of tachyarrhythmia upon detecting that the cardiac activity satisfies a third selected tachyarrhythmia criterion; and, making a final diagnosis of tachyarrhythmia if the sinus interval history count is less than a selected maximum sinus interval history count, and otherwise, inhibiting a final diagnosis of tachyarrhythmia.

2. The method as set forth in claim 1 and further including the steps of:

prescribing a tachycardia duration threshold;

computing an average interval duration of a selected number of intervals; and comparing the average interval duration with the prescribed tachycardia duration threshold;

wherein the first selected tachyarrhythmia criterion is that the average interval duration is shorter than the prescribed tachycardia duration threshold.

3. The method as set forth in claim 1 and further including the steps of:

prescribing a first tachycardia duration threshold;

prescribing a second tachycardia duration threshold;

computing an average interval duration of a selected number of intervals;

comparing the average interval duration with the prescribed first tachycardia duration threshold; and comparing the average interval duration with the prescribed second tachycardia duration threshold;

wherein the first selected tachyarrhythmia criterion is that the average interval duration is shorter than the prescribed first tachycardia duration threshold and longer than the prescribed second tachycardia duration threshold.

4. The method as set forth in claim 1 and further including the steps of:

prescribing a tachycardia duration threshold;

computing an average interval duration of a selected number of intervals;

comparing a selected interval of the selected number of intervals with the prescribed tachycardia duration threshold; and comparing the average interval duration with the prescribed tachycardia duration threshold;

wherein the second selected tachyarrhythmia criterion is satisfied if either the duration of the selected interval is greater than the prescribed tachycardia duration threshold, or the associated computed average interval duration is greater than the prescribed tachycardia duration threshold.

5. The method as set forth in claim 1 and further including the steps of:

setting a tachycardia interval maximum count limit;

prescribing a tachycardia duration threshold; and comparing each successive interval with the prescribed tachycardia duration threshold and counting the number of such comparisons for which the interval is shorter than the tachycardia duration threshold;

wherein the third selected tachyarrhythmia criterion is that the number of intervals which satisfy the criterion of the interval being shorter than the tachycardia duration threshold exceeds the maximum count limit before detection of a sinus rhythm.

6. A method for detecting cardiac arrhythmias, including the steps of:

detecting a patient's cardiac activity and initiating a tachyarrhythmia detection period upon detecting that the cardiac activity satisfies a first selected tachyarrhythmia criterion;

counting the number of intervals which satisfy a second selected tachyarrhythmia criterion, and producing a sinus interval history count indicative of the number of such intervals which are counted;

terminating the tachyarrhythmia detection period and making a preliminary diagnosis of tachyarrhythmia upon detecting that the cardiac activity satisfies a third selected tachyarrhythmia criterion;

determining if the preliminary diagnosis of tachyarrhythmia is proper according to a first measure of interval irregularity;

making a qualified preliminary diagnosis of tachyarrhythmia if it is determined that the preliminary diagnosis of tachyarrhythmia is proper according to the first measure of interval irregularity, and otherwise, inhibiting a final diagnosis of tachyarrhythmia; and, if a qualified preliminary diagnosis of tachyarrhythmia is made, then making a final diagnosis of tachyarrhythmia if the sinus interval history count is less than a selected maximum sinus interval history count, and otherwise, inhibiting a final diagnosis of tachyarrhythmia.

7. The method as set forth in claim 6 and further including the steps of:

prescribing a tachycardia duration threshold;

computing an average interval duration of a selected number of intervals; and comparing the average interval duration with the prescribed tachycardia duration threshold;

wherein the first selected tachyarrhythmia criterion is that the average interval duration is shorter than the prescribed tachycardia duration threshold.

8. The method as set forth in claim 6 and further including the steps of:

prescribing a first tachycardia duration threshold;

prescribing a second tachycardia duration threshold;

computing an average interval duration of a selected number of intervals;

comparing the average interval duration with the prescribed first tachycardia duration threshold; and comparing the average interval duration with the prescribed second tachycardia duration threshold with;

wherein the first selected tachyarrhythmia criterion is that the average interval duration is shorter than the prescribed first tachycardia duration threshold and longer than the prescribed second tachycardia duration threshold.

9. The method as set forth in claim 6 and further including the steps of:

prescribing a tachycardia duration threshold;

computing an average interval duration of a selected number of intervals;

comparing a selected interval of the selected number of intervals with the prescribed tachycardia duration threshold; and comparing the average interval duration with the prescribed tachycardia duration threshold;

wherein the second selected tachyarrhythmia criterion is satisfied if either the duration of the selected interval is greater than the prescribed tachycardia duration threshold, or the associated computed average interval duration is greater than the prescribed tachycardia duration threshold.

10. The method as set forth in claim 6 and further including the steps of:

setting a tachycardia interval maximum count limit;

prescribing a tachycardia duration threshold; and comparing each successive interval with the prescribed tachycardia duration threshold and counting the number of such comparisons for which the interval is shorter than the tachycardia duration threshold;

wherein the third selected tachyarrhythmia criterion is that the number of intervals which satisfy the criterion of the interval being shorter than the tachycardia duration threshold exceeds the maximum count limit before detection of a sinus rhythm.

11. A method for detecting cardiac arrhythmias, comprising the steps of:

monitoring an electrogram representative of a patient's cardiac activity including a sequence of cardiac events;

in response to the monitoring step, sensing intervals between successive cardiac events;

at every interval, determining the duration of that interval and computing the average duration of a prescribed number of preceding intervals, including that interval, and classifying that interval as either a countable tachyarrhythmia interval or a countable sinus interval, based upon the determined duration of that interval and the computed average duration associated with that interval, and further classifying that interval as an absolute sinus interval if either the duration of that interval or the computed average duration associated with that interval is greater than a prescribed duration threshold;

counting the number of absolute sinus intervals;

counting the number of countable tachyarrhythmia intervals and countable sinus intervals;

making a preliminary diagnosis of tachyarrhythmia if the counted number of countable tachyarrhythmia intervals exceeds a prescribed maximum tachyarrhythmia count before the counted number of countable sinus intervals exceeds a prescribed maximum sinus interval count; and, making a final diagnosis of tachyarrhythmia if the counted number of absolute sinus intervals is less than a prescribed maximum absolute sinus interval count, and otherwise, inhibiting diagnosis of tachyarrhythmia.

12. The method as set forth in claim 11, and further including the step following making a preliminary diagnosis of tachyarrhythmia of determining if the most recent average duration associated with the most recent countable tachyarrhythmia interval is greater than a selected rate overlap threshold and making a final diagnosis of tachyarrhythmia if the average duration is not greater than the rate overlap threshold and comparing the counted number of absolute sinus intervals with the prescribed maximum absolute sinus interval count to make a final diagnosis if the most recent average duration associated with the most recent countable tachyarrhythmia interval is greater than a selected rate overlap threshold.

13. A method for detecting cardiac arrhythmias, comprising the steps of:

monitoring an electrogram representative of a patient's cardiac activity including a sequence of cardiac events;

in response to the monitoring step, sensing intervals between successive cardiac events;

at every interval, determining the duration of that interval and computing the average duration of a prescribed number of preceding intervals, including that interval;

initiating a detection period upon detecting that the computed average duration is less than a prescribed average duration threshold;

at every interval after initiation of the detection period, classifying that interval as either a countable tachyarrhythmia interval or a countable sinus interval, based upon the determined duration of that interval and the computed average duration associated with that interval, and further classifying that interval as an absolute sinus interval if either the duration of that interval or the computed average duration associated with that interval is greater than a prescribed duration threshold;

counting the number of absolute sinus intervals;

counting the number of countable tachyarrhythmia intervals and countable sinus intervals;

terminating the detection period and making a preliminary diagnosis of tachyarrhythmia if the counted number of countable tachyarrhythmia intervals exceeds a prescribed maximum tachyarrhythmia count before the counted number of countable sinus intervals exceeds a prescribed maximum sinus interval count; and, making a final diagnosis of tachyarrhythmia if the counted number of absolute sinus intervals during the detection period is less than a prescribed maximum absolute sinus interval count, and otherwise, inhibiting diagnosis of tachyarrhythmia.

14. A method for detecting cardiac arrhythmias, comprising the steps of:

monitoring an electrogram representative of a patient's cardiac activity including a sequence of cardiac events;

in response to the monitoring step, sensing intervals between successive cardiac events;

at every interval, determining the duration of that interval and computing the average duration of a prescribed number of preceding intervals, including that interval, and classifying that interval as either a countable tachyarrhythmia interval or a countable sinus interval, based upon the determined duration of that interval and the computed average duration associated with that interval, and further classifying that interval as an absolute sinus interval if either the duration of that interval or the computed average duration associated with that interval is greater than a prescribed duration threshold;

counting the number of absolute sinus intervals;

counting the number of countable tachyarrhythmia intervals and countable sinus intervals;

determining if the preliminary diagnosis of tachyarrhythmia is proper according to a first measure of interval irregularity;

making a qualified preliminary diagnosis of tachyarrhythmia if it is determined that the preliminary diagnosis of tachyarrhythmia is proper according to the first measure of interval irregularity, and otherwise, inhibiting a final diagnosis of tachyarrhythmia; and, if a qualified preliminary diagnosis of tachyarrhythmia is made, then making a final diagnosis of tachyarrhythmia if the counted number of absolute sinus intervals during the tachyarrhythmia detection period is less than a selected maximum sinus interval count, and otherwise, inhibiting a final diagnosis of tachyarrhythmia.

15. A method for detecting cardiac arrhythmias, comprising the steps of:

detecting a patient's cardiac activity;

counting the number of intervals which satisfy a first selected tachyarrhythmia criterion, and producing a sinus interval history count indicative of the number of such intervals which are counted;

making a preliminary diagnosis of tachyarrhythmia upon detecting that the cardiac activity satisfies a second selected tachyarrhythmia criterion; and, making a final diagnosis of tachyarrhythmia if the sinus interval history count is less than a selected maximum sinus interval history count, and otherwise, inhibiting a final diagnosis of tachyarrhythmia.

16. The method of claim 15 and further including the steps following the step of making a preliminary diagnosis of:

determining a first measure of interval irregularity by comparing during a tachycardia detection period the relative number of sinus intervals and tachyarrhythmia intervals wherein said first measure of interval irregularity is consistent with a diagnosis of tachyarrhythmia if there are more tachyarrhythmia intervals than sinus intervals by at least a small number;

determining if the preliminary diagnosis of tachyarrhythmia is consistent with the determination based upon the first measure of interval irregularity; and making a qualified preliminary diagnosis of tachyarrhythmia if it is determined that the preliminary diagnosis of tachyarrhythmia is consistent with the determination based upon the first measure of interval irregularity, and otherwise, inhibiting a final diagnosis of tachyarrhythmia.

17. A method of discriminating between supraventricular tachycardia and ventricular tachycardia comprising the steps of:

detecting a patient's cardiac activity and measuring successive cardiac interval durations;

comparing each cardiac interval to a selected tachycardia threshold and identifying an interval as a tachycardia interval if its duration is less than the tachycardia threshold;

initiating a tachycardia detection period upon identifying a tachycardia interval;

for each interval during said tachycardia detection period, computing the average duration of a selected number of intervals, including that interval;

during said tachycardia detection period counting the number of intervals which have a duration greater than the selected tachycardia threshold or for which the computed average duration is greater the selected tachycardia threshold, to produce a sinus interval history count indicative of the number of such intervals which are counted;

terminating said tachycardia detection period when a selected number of tachycardia intervals have been detected; and diagnosing a ventricular tachycardia if said sinus interval history count is less than a selected sinus interval history count threshold and diagnosing a supraventricular tachycardia if said sinus interval history count is greater than or equal to said selected sinus interval history count threshold.

* * * * *